(12) United States Patent
Yin

(10) Patent No.: US 10,689,361 B2
(45) Date of Patent: Jun. 23, 2020

(54) QUINOLINE DERIVATIVE AND USE THEREOF

(71) Applicant: Jianming Yin, Hangzhou (CN)

(72) Inventor: Jianming Yin, Hangzhou (CN)

( * ) Notice: Subject to any disclaimer, the term of this patent is extended or adjusted under 35 U.S.C. 154(b) by 0 days.

(21) Appl. No.: 16/266,000

(22) Filed: Feb. 2, 2019

(65) Prior Publication Data

US 2019/0169163 A1    Jun. 6, 2019

Related U.S. Application Data

(63) Continuation-in-part of application No. PCT/CN2017/096569, filed on Aug. 9, 2017.

(30) Foreign Application Priority Data

Aug. 9, 2016    (CN) .......................... 2016 1 0649732

(51) Int. Cl.
| | | |
|---|---|---|
| *C07D 401/12* | (2006.01) | |
| *A61P 35/00* | (2006.01) | |
| *A61K 31/4709* | (2006.01) | |
| *A61K 31/47* | (2006.01) | |
| *A61P 9/00* | (2006.01) | |
| *C07D 215/46* | (2006.01) | |
| *C07D 215/233* | (2006.01) | |
| *C07D 215/48* | (2006.01) | |

(52) U.S. Cl.
CPC ............ *C07D 401/12* (2013.01); *A61K 31/47* (2013.01); *A61K 31/4709* (2013.01); *A61P 9/00* (2018.01); *A61P 35/00* (2018.01); *C07D 215/233* (2013.01); *C07D 215/46* (2013.01); *C07D 215/48* (2013.01)

(58) Field of Classification Search
None
See application file for complete search history.

(56) References Cited

U.S. PATENT DOCUMENTS

| | | |
|---|---|---|
| 6,821,987 B2 | 11/2004 | Kubo et al. |
| 7,612,092 B2 | 11/2009 | Funahashi et al. |
| 7,973,160 B2 | 7/2011 | Funahashi et al. |
| 8,304,427 B2 | 11/2012 | Suda et al. |
| 2011/0034439 A1 | 2/2011 | Suda et al. |
| 2013/0225581 A1 | 8/2013 | Furuta et al. |
| 2014/0018365 A1 | 1/2014 | Schultz-Fademrecht et al. |

FOREIGN PATENT DOCUMENTS

| | | | |
|---|---|---|---|
| CN | 103405429 A | 11/2013 | |
| WO | 2012008564 A1 | 1/2012 | |
| WO | WO-2012008563 A1 * | 1/2012 | ........... C07D 401/12 |
| WO | 2013180949 A1 | 12/2013 | |

OTHER PUBLICATIONS

Wu et al.,Toxicology, 236, pp. 1-6, (Year: 2007).*
Internation Search Report of PCT/CN2017/096569, dated Nov. 2, 2017.

* cited by examiner

*Primary Examiner* — Zinna Northington Davis
(74) *Attorney, Agent, or Firm* — ZANIP

(57) ABSTRACT

Provided are a novel quinoline derivative, or a pharmaceutically acceptable salt, a hydrate, or a metabolite formed by metabolism in any form thereof, and use thereof in preparing a medicine for preventing and/or treating indications associated with angiogenesis. The quinoline derivative is an ideal and high-efficiency VEGFR inhibitor, and is able to be used to treat or prevent tumour growth and other metastasis growth diseases associated with angiogenesis.

7 Claims, No Drawings

QUINOLINE DERIVATIVE AND USE THEREOF

CROSS-REFERENCE TO RELATED APPLICATIONS

This application is a continuation-in-part of International Patent Application No. PCT/CN2017/096569 with a filing date of Aug. 9, 2017, designating the United States, now pending, and further claims priority to Chinese Patent Application No. 201610649732.2 with a filing date of Aug. 9, 2016. The content of the aforementioned application, including any intervening amendments thereto, is incorporated herein by reference.

TECHNICAL FIELD OF THE INVENTION

The present disclosure relates to a quinoline derivative, and use thereof in preparing a medicine for preventing and/or treating indications associated with angiogenesis.

BACKGROUND OF THE INVENTION

Angiogenesis is the growth of new capillary blood vessels in existing capillaries and postcapillary venule, which is a complex process involving multiple molecules of various cells.

Vascular endothelial growth factor (VEGF) is a vascular endothelial cell-specific heparin-binding growth factor that induces angiogenesis in vivo. The expression of VEGF is closely related to the density of microvessels in the tissue and the number of new blood vessels. The VEGF receptor (VEGFR) family includes VEGFR-1, VEGFR-2 and VEGFR3.

Angiogenesis plays an important role in the development and metastasis of tumors, and inhibition of this process can significantly prevent the development, spread and metastasis of tumor tissue. Inhibition of VEGFR can treat tumor growth, as well as other angiogenesis-related metastatic growth diseases such as psoriasis, Kaposi's sarcoma, restenosis such as stent-induced restenosis, endometriosis, Crohn's disease, Hodgkin's disease, leukemia, arthritis, hemangioma, angiofibroma, eye diseases such as diabetic retinopathy and neovascular glaucoma, nephropathy such as glomerulonephritis, diabetic nephropathy, malignant nephrosclerosis, thrombotic microangiopathy syndrome, transplant rejection and glomerulopathy, fibrotic diseases such as cirrhosis, glomerular mesangial cell proliferative diseases, arteriosclerosis, nerve tissue damage, senile keratosis, and the like.

SUMMARY OF THE INVENTION

The technical solution to be solved by the present disclosure is to provide a quinoline derivative, or a pharmaceutically acceptable salt, a hydrate, or a metabolite formed by metabolism in any form thereof, which is an ideal VEGFR inhibitor.

The present disclosure further provides use of the quinoline derivative, or the pharmaceutically acceptable salt, the hydrate, or the metabolite formed by metabolism in any form thereof in preparing a medicine for preventing and/or treating indications associated with angiogenesis.

To solve the above problems, the present disclosure employs the following technical solution:

A quinoline derivative having a structure represented by Formula (I), or a pharmaceutically acceptable salt, a hydrate, or a metabolite formed by metabolism in any form thereof,

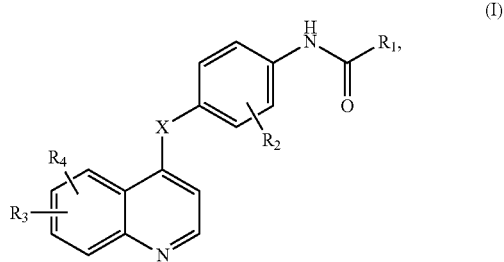

wherein:
$R_1$ is $R_5$ or $NHR_5$, wherein $R_5$ is selected from cycloalkyl, heterocyclic and substituted heterocyclic;

$R_2$ is selected from hydrogen, halogen, hydroxy, alkoxy and cyano;

$R_3$ and $R_4$ are independently selected from $OR_6$, $C(O)NH_2$ and $C(O)NHR_6$, wherein $R_6$ is $C_1$-$C_6$ alkyl or halogenated alkyl;

X is selected from NH and O;

non-exchangeable hydrogen is unsubstituted, or partially or fully substituted by deuterium in the quinoline derivative having the structure represented by Formula (I), or the pharmaceutically acceptable salt, the hydrate, or the metabolite formed by metabolism in any form thereof.

In the present disclosure, $R_2$ is preferably Cl or F.

In the present disclosure, $R_5$ is preferably cycloalkyl or halogenated cycloalkyl; or $R_5$ is preferably heterocyclic containing N or O, which is unsubstituted or substituted by one or more substituents selected from halogen and $C_1$-$C_6$ alkyl, wherein carbon number of the cycloalkyl is preferably 3 to 6. More preferably, $R_5$ is cycloalkyl having a carbon number of 3; or $R_5$ is five- or six-membered unsaturated heterocycle containing 1 or 2 or 3 N, which is unsubstituted or substituted by one or two substituents selected from methyl and ethyl.

Further more preferably, $R_5$ is cycloalkyl having a carbon number of 3; or $R_5$ is 5-membered unsaturated heterocycle containing 2 N, which is unsubstituted or substituted by one methyl.

According to some preferred implementations of the present disclosure, $R_5$ is

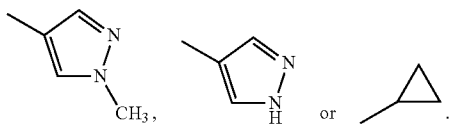

In the present disclosure, $R_6$ is preferably methyl or ethyl.

In the present disclosure, the representative compound of the quinoline derivative is one of compounds represented by the following structural formulas:

Il

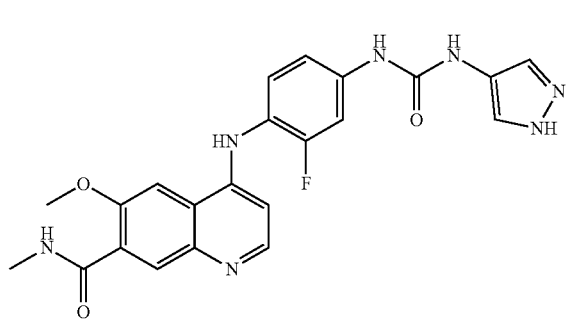

Im

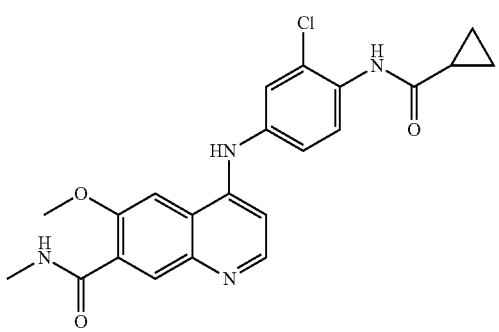

In

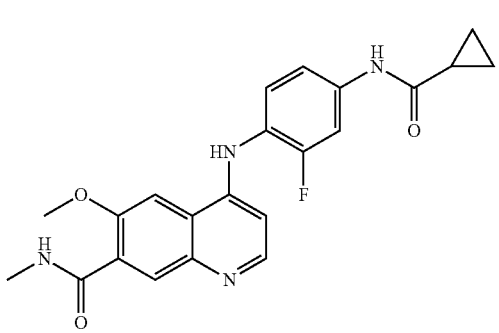

Io

Ip

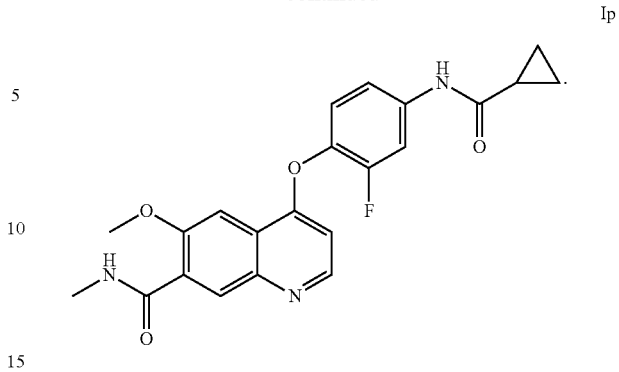

According to the present disclosure, the compound of the quinoline derivative includes not only a single compound form, but also a mixture of a plurality of compounds of which structures meet the requirements of Formula (I), and as well as different isomers of a same compound, such as racemates, enantiomers, diastereomers and the like. The pharmaceutically acceptable salt includes, but is not limited to, hydrochloride, phosphate, sulfate, acetate, maleate, methanesulfonate, besylate, benzoate, toluenesulfonate, succinate, fumarate, fumarate, tartrate, gallate, citrate, and the like. "Prodrug of a compound of Formula (I)" means a substance which, upon administration by a suitable method, can be converted into at least one of compounds of Formula (I) or salts thereof by metabolism or chemical reaction in volunteers.

The preparation of the quinoline derivative of the present disclosure can be carried out by synthetic routes to those analogous methods well known in the chemical art, in particular the compounds of the present disclosure are synthesized according to the description contained herein. The reagents are generally obtained from commercial sources or are readily prepared using methods well known to those skilled in the art.

Another technical solution of the present disclosure is: a quinoline derivative intermediate which is one of compounds represented by the following structural formulas:

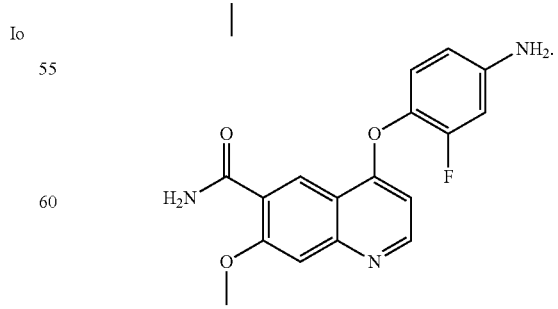

Yet another technical solution employed by the present disclosure is: use of the quinoline derivative, or the pharmaceutically acceptable salt, the hydrate, or the metabolite formed by metabolism in any form thereof mentioned above in preparing a medicine for preventing and/or treating indications associated with angiogenesis.

The indications associated with angiogenesis include malignant tumor diseases.

The malignant tumor diseases include lung cancer, mesothelioma, gastrointestinal cancer, breast cancer, pancreatic cancer, bladder cancer, ovarian cancer, esophageal cancer, head and neck cancer, colon cancer, skin cancer, prostate cancer, cervical cancer, lymphoma, leukemia, melanoma, glioma, nasopharyngeal cancer, and the like.

The indications associated with angiogenesis further include other angiogenesis-related metastatic growth diseases, such as psoriasis, Kaposi's sarcoma, restenosis such as stent-induced restenosis, endometriosis, Crohn's disease, Hodgkin's disease, leukemia, arthritis, hemangioma, angiofibroma, eye diseases such as diabetic retinopathy and neovascular glaucoma, nephropathy such as glomerulonephritis, diabetic nephropathy, malignant nephrosclerosis, thrombotic microangiopathy syndrome, transplant rejection and glomerulopathy, fibrotic diseases such as cirrhosis, glomerular mesangial cell proliferative diseases, arteriosclerosis, nerve tissue damage, senile keratosis, and the like.

Yet another technical solution employed by the present disclosure is: a medicine for preventing and/or treating indications associated with angiogenesis, contains the quinoline derivative of Formula (1), or the pharmaceutically acceptable salt, the hydrate, or the metabolite formed by metabolism in any form thereof mentioned above.

Due to the use of the above technical solutions, the present disclosure has the following advantages over the prior art:

The compounds provided by the present disclosure are novel quinoline derivatives, which are ideal and high-efficiency VEGFR inhibitors, and can inhibit angiogenesis by acting on VEGFR, and have a certain therapeutic effect on angiogenesis-related diseases. Therefore, the compounds of the present disclosure can be used for the preparation of a medicine for treating or preventing various indications related to angiogenesis, and can also enhance the anti-tumor effect of other drugs by inhibiting angiogenesis.

DETAILED DESCRIPTION OF EXEMPLARY EMBODIMENTS

In the following, the present disclosure is further explained in detail combining with specific embodiments, but is not limited to the following embodiments.

Embodiment 1

The present embodiment provides Compound of Formula Ia, with the following chemical structure:

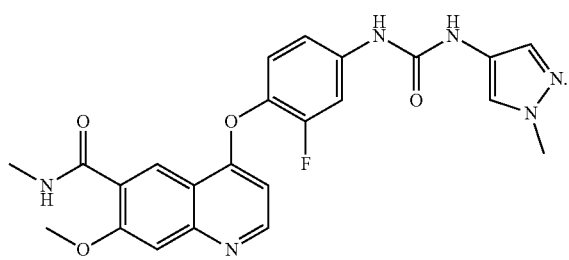 [SMILES: CNC(=O)c1cc2c(Oc3ccc(NC(=O)Nc4cnn(C)c4)cc3F)ccnc2cc1OC]

Compound of Formula Ia can be obtained through the following synthetic route:

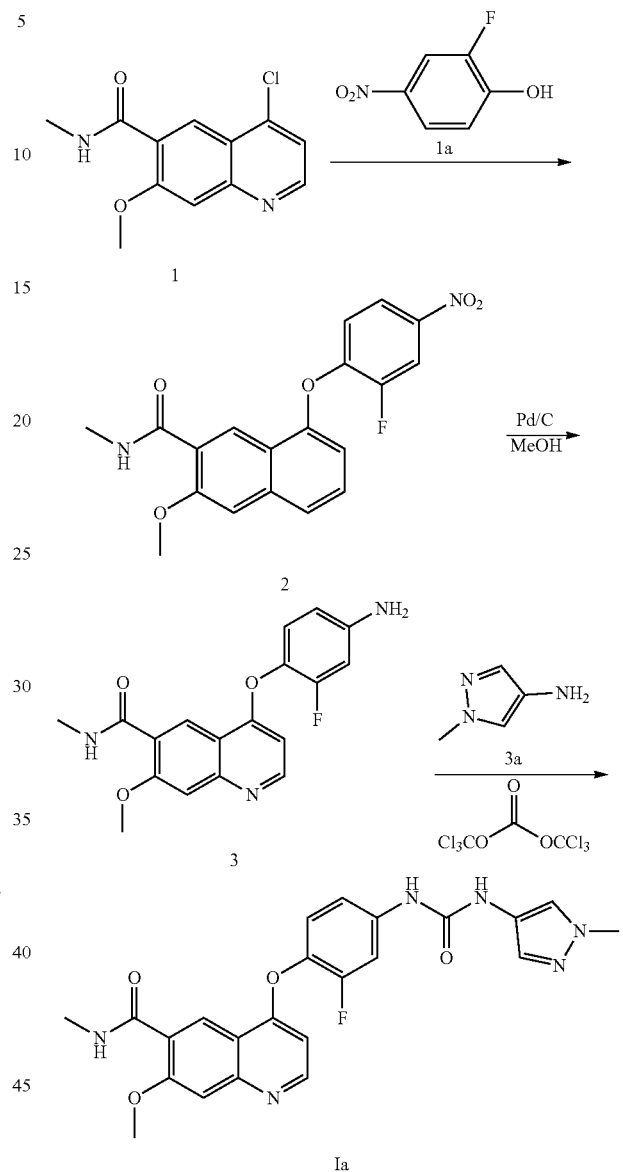

Preparation method of Compound of Formula Ia specifically comprises the following steps:

(1) Preparation of Intermediate 2: Compound 1 (500 mg, 2 mmol), NMP (20 mL), Compound 1a (471 mg, 3 mmol) and DIPEA (774 mg, 6 mmol) were sequentially added to a 50 mL reaction bottle. The mixture was heated to 160° C. and stirred for 2 hours. After cooling, the solution was concentrated and purified by silica gel column chromatography to give Intermediate 2 (0.4 g, 1.08 mmol, 56% yield) as a gray solid.

(2) Preparation of Intermediate 3: Intermediate 2 (400 mg, 1.08 mmol), MeOH (80 mL) and palladium-carbon (5%, 100 mg) were sequentially added to a 250 mL reaction bottle. The reaction mixture was stirred at room temperature for 3 hours under hydrogen atmosphere. The reaction mixture was filtered, and the filtrate was concentrated to give Intermediate 3 (0.3 g, 0.88 mmol, 80% yield) as a white solid. LCMS showed a molecular ion peak m/z[MH]$^+$: 342.2.

(3) Preparation of Compound of Formula Ia: Intermediate 3 (0.3 g, 0.88 mmol) and dry THF (20 mL) were sequentially added to a 50 mL three-necked flask. Under nitrogen protection, the reaction mixture was cooled to 0° C., and slowly added with DIPEA (0.227 g, 1.76 mmol) dropwise. The reaction mixture was stirred for 1 hour at 0° C. Triphosgene (90 mg, 0.3 mmol) was added to the reaction mixture. The reaction mixture was stirred for 3 hours at 0° C. Then Compound 3a (94 mg, 0.97 mmol) was quickly added to the reaction solution. The reaction mixture was stirred at room temperature overnight, concentrated, and purified by HPLC to give Compound of Formula Ia (0.12 g, 0.26 mmol, 29% yield) as a white solid.

The obtained target product Compound of Formula Ia was identified by hydrogen nuclear magnetic resonance $^1$H-NMR (400 MHz, d-DMSO) and mass spectrometry, and the results are as follows:

Absorption peaks in $^1$H-NMR spectrum: δ=8.99 (s, 1H, ArH), 8.65 (d, J=5.2 Hz, 1H, ArH), 8.59 (s, 1H, ArH), 8.51 (s, 1H, ArH), 8.37-8.36 (m, 1H, CONHCH$_3$), 7.74-7.71 (m, 2H, CONH, ArH), 7.50 (s, 1H, ArH), 7.39-7.34 (m, CONH, ArH), 7.23 (d, J=8.8 Hz, 1H, ArH), 6.48 (d, J=4.8 Hz, 1H, ArH), 4.00 (s, 3H, NCH$_3$), 3.77 (s, 3H, OCH$_3$), 2.82 (d, J=4.8 Hz, 3H, CONHCH$_3$). m/z[MH]$^+$: 465.2. The product was calculated to have the molecular formula C$_{23}$H$_{21}$FN$_6$O$_4$, and the exact mass was 464.16.

Embodiment 2

The present embodiment provides Compound of Formula Ib, with the following chemical structure:

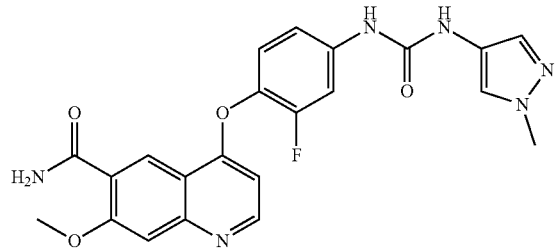 [SMILES: COc1cc2nccc(Oc3ccc(NC(=O)Nc4cnn(C)c4)cc3F)c2cc1C(N)=O]

Compound of Formula Ib can be obtained through the following synthetic route:

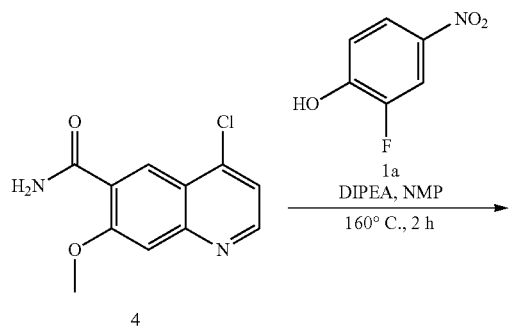

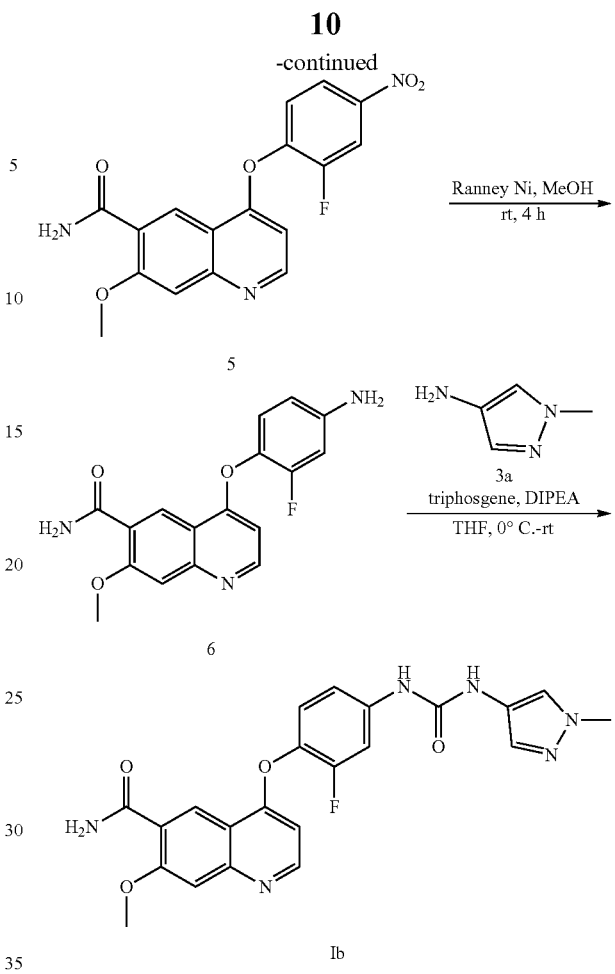

Preparation method of Compound of Formula Ib specifically comprises the following steps:

(1) Preparation of Intermediate 5: Compound 4 (1.8 g, 7.63 mmol), NMP (40 mL), Compound 1a (1.797 g, 11.45 mmol) and DIPEA (5.9 g, 45.78 mmol) were sequentially added to a 150 mL three-necked flask. The mixture was heated to 160° C. for 2 hours. After cooling to room temperature, the reaction mixture was added to water to precipitate a solid. The mixture was filtered, and the filter cake was washed with water and dried to give Intermediate 5 (2.2 g, 80% yield) as a gray solid. LCMS showed a molecular ion peak m/z[MH]$^+$: 358.1.

(2) Preparation of Intermediate 6: Intermediate 5 (700 mg, 1.96 mmol), MeOH (200 mL) and Raney nickel (700 mg) were sequentially added to a 500 mL three-necked flask. The reaction mixture was stirred at room temperature for 3 hours under hydrogen atmosphere. The reaction mixture was filtered, and the filtrate was concentrated and dried to give Intermediate 6 (620 mg, 96.7% yield) as a light brown solid. LCMS showed a molecular ion peak m/z[MH]$^+$: 328.1.

(3) Preparation of Compound of Formula Ib: Intermediate 6 (163 mg, 0.5 mmol), triphosgene (49 mg, 0.165 mmol) and dry THF (5 mL) were sequentially added to a 10 mL three-necked flask. Under nitrogen protection, the reaction mixture was cooled to 0° C., and slowly added with DIPEA (194 mg, 1.5 mmol) dropwise. The reaction mixture was stirred for 10 min. Then Compound 3a (62 mg, 0.5 mmol) was quickly added to the reaction mixture. The reaction mixture was stirred at room temperature overnight, concentrated, and purified by reversed phase column chromatography and HPLC to give Compound of Formula Ib (38 mg, 16.9% yield) as a white solid.

The obtained target product Compound of Formula Ib was identified by hydrogen nuclear magnetic resonance $^1$H-NMR (400 MHz, d-DMSO) and mass spectrometry, and the results are as follows:

Absorption peaks in $^1$H-NMR spectrum: δ=9.16 (s, 1H, ArH), 8.85 (d, J=6 Hz, 1H, ArH), 8.72 (s, 1H, ArH), 8.67 (s, 1H, ArH), 7.95 (b, 1H, CONH$_2$), 7.86 (b, 1H, CONH$_2$), 7.80 (dd, 1H, J$_1$=2.4 Hz, J$_2$=13.2 Hz, ArH), 7.76 (s, 1H, ArH), 7.59 (s, 1H, CONH), 7.45 (t, J=8.8 Hz, 1H, ArH), 7.40 (s, 1H, CONH), 7.30-7.28 (m, 1H, ArH), 6.76 (d, J=6 Hz, 1H, ArH), 4.07 (s, 3H, NCH$_3$), 3.79 (s, 3H, OCH$_3$).

m/z[MH]+: 451.2. The product was calculated to have the molecular formula C$_{22}$H$_{19}$FN$_6$O$_4$, and the exact mass was 450.15.

Embodiment 3

The present embodiment provides Compound of Formula Ic, with the following chemical structure:

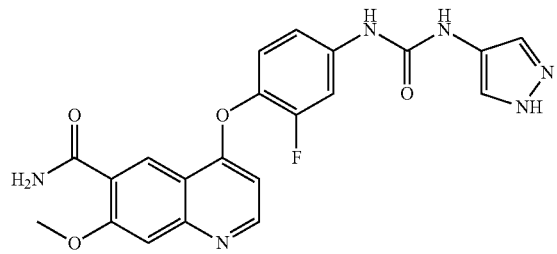 [SMILES: COc1cc2nccc(Oc3ccc(NC(=O)Nc4cn[nH]c4)cc3F)c2cc1C(N)=O]

Compound of Formula Ic can be obtained through the following synthetic route:

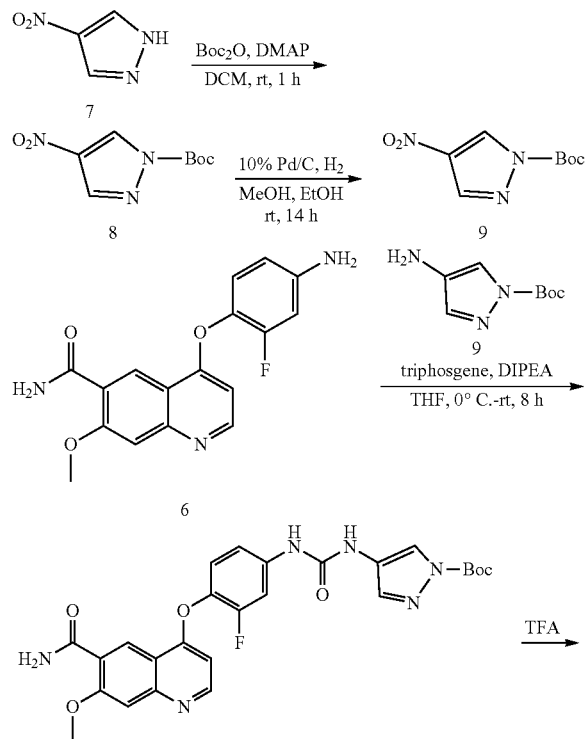

Ic

Preparation method of Compound of Formula Ic specifically comprises the following steps:

(1) Preparation of Intermediate 8: Compound 7 (11.3 g, 100 mmol), DMAP (2.44 g, 20 mmol) and DCM (140 mL) were sequentially added to a 500 mL three-necked flask. (Boc)$_2$O (26 g, 120 mmol) was dissolved in DCM (40 mL), and the solution was added into the three-necked flask slowly. The reaction mixture was stirred for 1 hours at room temperature. The reaction mixture was washed with 0.5 N HCl (150 mL) twice, washed with saturated salt solution, dried over Na$_2$SO$_4$ and concentrated to give Intermediate 8 (20 g, 93.8% yield) as a white solid.

(2) Preparation of Intermediate 9: Intermediate 8 (10 g, 46.9 mmol), MeOH (200 mL), EtOH (100 mL) and 10% Pd/C (2 g) were sequentially added to a 250 mL three-necked flask. The reaction mixture was stirred at room temperature for 14 hours under hydrogen atmosphere. The reaction mixture was filtered, and the filtration cake was dried to give Intermediate 9 (8.0 g, 93.2% yield) as a light purple solid.

(3) Preparation of Compound of Formula Ic: Intermediate 6 (220 mg, 0.67 mmol), triphosgene (66 mg, 0.22 mmol) and dry THF (5 mL) were sequentially added to a 10 mL three-necked flask. Under nitrogen protection, the reaction mixture was cooled to 0° C., and slowly added with DIPEA (173 mg, 1.34 mmol) dropwise. The reaction mixture was stirred for 10 min. Then Intermediate 9 (240 mg, 1.34 mmol) was quickly added to the reaction mixture. The reaction mixture was stirred at room temperature overnight, concentrated, and purified by reversed phase column chromatography to give Intermediate 10 (95 mg, 32.4% yield) as a white solid. Because of there is TFA in solution, Intermediate 10 is converted to Compound of Formula Ic during lyophilization.

The obtained target product Compound of Formula Ic was identified by hydrogen nuclear magnetic resonance $^1$H-NMR (400 MHz, d-DMSO) and mass spectrometry, and the results are as follows:

Absorption peaks in $^1$H-NMR spectrum: δ=9.17-9.14 (m, 1H, ArH), 8.90-8.89 (m, 1H, ArH), 8.73 (s, 1H, ArH), 8.65-8.62 (m, 1H, ArH), 7.97 (b, 1H, CONH$_2$), 7.88 (b, 1H, CONH$_2$), 7.82 (dd, 1H, J$_1$=2.0 Hz, J$_2$=13.6 Hz, ArH), 7.63 (s, 2H, NHCONH), 7.59 (m, 1H, ArH), 7.46 (t, J=8.8 Hz, 1H, ArH), 7.32-7.29 (m, 1H, ArH), 6.83-6.82 (m, 1H, ArH), 4.07 (s, 3H, OCH$_3$). m/z[MH]$^+$: 437.2. The product was calculated to have the molecular formula C$_{21}$H$_{17}$FN$_6$O$_4$, and the exact mass was 436.13.

Embodiment 4

The embodiment provides an enzymatic activity test of compounds.

1. Test Method

The semi-inhibitory concentration $IC_{50}$ (the concentration of the compound required to inhibit the enzymatic activity to 50%) of a compound was measured by mixing a fixed enzyme with a specific substrate and the test compound of different concentrations. The test method used was Caliper Mobility Shift Assay, the kinases tested were VEGFR1, VEGFR2, VEGFR3, FLT3, PDGFR$_\alpha$, PDGFR$_\beta$, FGFR1, RET, EGFR and IGF1R, and the standard reference compound used was staurosporine.

2. Test Results

Table 1 summarizes the experimental results of inhibition of the target compounds (Ia, Ib and Ic) against VEGFR1, VEGFR2, VEGFR3, FLT3, PDGFR$_\alpha$, PDGFR$_\beta$, FGFR1, RET, EGFR and IGF1R enzyme activities, and the results showed that the target compounds had strong inhibitory activity against VEGFR2, and had good selective inhibitory activity against other related kinases, especially EGFR and IGF1R. This selective inhibiting effect on VEGFR2 has important therapeutic implications for angiogenesis-related indications including malignant neoplastic disease and other angiogenesis-related metastatic growth disease. Table 1 also summarizes data of regorafenib, an effective VEGFR2 inhibitor currently available in the market.

TABLE 1 experiment results of enzymatic activity inhibition of the compounds

| Kinase | Kinase inhibitory activity ($IC_{50}$, nM) | | | |
| --- | --- | --- | --- | --- |
| | Compound of Formula Ia | Compound of Formula Ib | Compound of Formula Ic | Regorafenib |
| VEGFR1 | 381 | 555 | 831 | 185 |
| VEGFR2 | 2.4 | 3 | 11 | 34 |
| VEGFR3 | 56 | 84 | 34 | 43 |
| FLT3 | 576 | 890 | 708 | 178 |
| PDGFR$_\alpha$ | 27 | 37 | 42 | 26 |
| PDGFR$_\beta$ | 110 | 165 | 151 | 67 |
| FGFR1 | >1000 | >1000 | >1000 | 298 |
| RET | 106 | 290 | 204 | 35 |
| EGFR | >500000 | >200000 | >200000 | 10606 |
| IGF1R | >500000 | >200000 | >200000 | >400000 |

Embodiment 5

This embodiment provides a pharmacokinetic property evaluation test.

1. Experimental Method

Experimental animals: CD-1 mice, males and females; weight: 20-25 g;

Preparation of the test sample: The target compound was formulated into 0.2 mg/mL for use. Route of administration: intravenous injection. Dosing capacity and frequency: 2 mL/kg, single administration. Dosage: 3 mg/kg.

Sample collection: Blood was collected at the following time points: 5 min, 15 min, 30 min, 1 hr, 2 hr, 4 hr, 8 hr, and 24 hr after administration.

2. Sample Analysis and Results

Sample analysis: The collected samples were tested using the LC-MS/MS method. The instrument model was API4000.

Pharmacokinetic data analysis: The obtained plasma concentration data were fitted and calculated according to the non-compartment model using WinNolin, and some results are summarized in Table 2.

TABLE 2

Pharmacokinetic parameters of target compounds calculated according to the non-compartment model

| Pharmacokinetic parameters (Unit) | Compound of Formula Ia | Compound of Formula Ib |
| --- | --- | --- |
| CL (L/hr/kg) | 1.51 | 1.83 |
| Vss (L/kg) | 0.525 | 1.48 |
| Terminal $t_{1/2}$ (hr) | 0.47 | 2.24 |
| $AUC_{last}$ (hr*ng/mL) | 2042 | 1605 |
| $MRT_{INF}$ (hr) | 0.34 | 0.82 |

The results of the tests indicate that the compounds of the present disclosure have pharmacokinetic characteristics comparable to those of the therapeutic route.

The above embodiments are merely representative. As can be seen from the above embodiments, the compounds of the present disclosure are ideal highly effective and selective VEGFR2 kinase inhibitors, and can be expected to be used for the treatment or prevention of angiogenesis-related indications including malignant tumor diseases and other angiogenesis-related metastatic growth diseases and get very good results, and can also be combined with different types of pharmaceutical salts to prepare oral preparations (tablets or capsules, etc.). A tablet or capsule made with a compound of the present disclosure can be taken one or more times a day. The compounds of the present disclosure can also be combined with other drugs to prepare a compound preparation or a topical preparation.

The embodiments described above are only for illustrating the technical concepts and features of the present disclosure, and are intended to make those skilled in the art being able to understand the present disclosure and thereby implement it, and should not be concluded to limit the protective scope of this disclosure. Any equivalent variations or modifications according to the present disclosure should be covered by the protective scope of the present disclosure.

I claim:

1. A quinoline derivative having a structure represented by Formula (I), a pharmaceutically acceptable salt, or a hydrate, thereof,

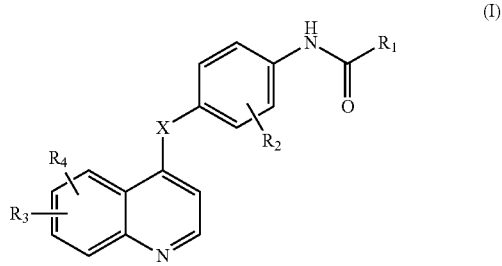

wherein:
$R_1$ is $NHR_5$, wherein $R_5$ is five-membered unsaturated heterocycle containing 2 N, which is substituted by one methyl;
$R_2$ is selected from hydrogen, halogen, hydroxy, alkoxy and cyano;

$R_3$ and $R_4$ are independently selected from $OR_6$, $C(O)NH_2$ and $C(O)NHR_6$, wherein $R_6$ is $C_1$-$C_6$ alkyl or halogenated alkyl;

X is selected from O;

non-exchangeable hydrogen is unsubstituted, or partially or fully substituted by deuterium in the quinoline derivative having the structure represented by Formula (I), or the pharmaceutically acceptable salt, or the hydrate thereof.

2. The quinoline derivative, the pharmaceutically acceptable salt, or the hydrate thereof according to claim 1, wherein $R_2$ is Cl or F.

3. The quinoline derivative, the pharmaceutically acceptable salt, or the hydrate thereof according to claim 1, wherein $R_3$ and $R_4$ are independently selected from $OR_6$ and $C(O)NH_2$, the $R_6$ is methyl or ethyl.

4. The quinoline derivative, the pharmaceutically acceptable salt, or the hydrate, thereof according to claim 1, wherein $R_5$ is 5. The quinoline derivative, the pharmaceutically acceptable salt, or the hydrate thereof according to claim 1, wherein $R_3$ and $R_4$ are independently selected from $C(O)NH_2$ and $C(O)NHR_6$, the $R_6$ is methyl or ethyl.

6. The quinoline derivative, the pharmaceutically acceptable salt, or the hydrate thereof according to claim 1, wherein the quinoline derivative is the compound represented by the following structural formula, (Ib)

7. A medicine for preventing and/or treating indications associated with angiogenesis, containing the quinoline derivative, the pharmaceutically acceptable salt, or the hydrate thereof according to claim 1.

* * * * *